US012740946B2

(12) United States Patent
Lin et al.

(10) Patent No.: US 12,740,946 B2
(45) Date of Patent: Sep. 22, 2026

(54) SPINNING SOLUTION, AND ALGINATE FIBER COMPRISING CANNABIDIOL, METHOD FOR PRODUCING THE SAME, AND USE THEREOF

(71) Applicant: PELL BIO-MED TECHNOLOGY CO., LTD., Taipei City (TW)

(72) Inventors: Chen-Lung Lin, Kaohsiung City (TW); Wen-Pin Chien, Taipei City (TW)

(73) Assignee: PELL BIO-MED TECHNOLOGY CO., LTD., Taipei City (TW)

( * ) Notice: Subject to any disclaimer, the term of this patent is extended or adjusted under 35 U.S.C. 154(b) by 820 days.

(21) Appl. No.: 17/974,927

(22) Filed: Oct. 27, 2022

(65) Prior Publication Data

US 2023/0134465 A1 May 4, 2023

(30) Foreign Application Priority Data

Oct. 29, 2021 (TW) ................................ 110140458

(51) Int. Cl.

| | |
|---|---|
| ***A61K 9/70*** | (2006.01) |
| ***A01N 25/10*** | (2006.01) |
| ***A01N 31/16*** | (2006.01) |
| ***A61K 31/00*** | (2006.01) |
| ***A61P 29/00*** | (2006.01) |
| ***A61P 37/08*** | (2006.01) |
| ***A61P 39/06*** | (2006.01) |
| ***D01D 1/10*** | (2006.01) |
| ***D01D 5/06*** | (2006.01) |
| ***D01F 1/10*** | (2006.01) |
| ***D01F 9/04*** | (2006.01) |

(52) U.S. Cl.
CPC ................ *A61K 9/70* (2013.01); *A01N 25/10* (2013.01); *A01N 31/16* (2013.01); *A61K 31/658* (2023.05); *A61P 29/00* (2018.01); *A61P 37/08* (2018.01); *A61P 39/06* (2018.01); *D01D 1/106* (2013.01); *D01D 5/06* (2013.01); *D01F 1/10* (2013.01); *D01F 9/04* (2013.01); *D10B 2509/00* (2013.01)

(58) Field of Classification Search
CPC . A61K 9/70; A61K 31/05; A61P 39/06; A61P 37/08; A61P 29/00; A61N 31/16; D01D 1/106; D01F 1/10; D01B 2509/00
See application file for complete search history.

(56) References Cited

U.S. PATENT DOCUMENTS

| | | |
|---|---|---|
| 2019/0328678 A1 | 10/2019 | Sunderland |
| 2021/0205224 A1 | 7/2021 | Noel |
| 2021/0259985 A1 | 8/2021 | Hall |

FOREIGN PATENT DOCUMENTS

| | | | | |
|---|---|---|---|---|
| CN | 105176026 A | 12/2015 | | |
| CN | 113152094 A | 7/2021 | | |
| JP | H08-013251 A | 1/1996 | | |
| JP | H10-502838 A | 3/1998 | | |
| JP | 2021522421 | 8/2021 | | |
| RU | 2591704 C2 * | 7/2016 | ............... | D04H 3/00 |
| TW | 201524538 A | 7/2015 | | |
| WO | WO-9602284 A1 * | 2/1996 | ............. | A61L 15/46 |
| WO | WO2021092054 A1 | 5/2021 | | |
| WO | WO2021161250 A1 | 8/2021 | | |

OTHER PUBLICATIONS

Tianzhu, Jia and Ning, Xu, Science of Processing Chinese Materia Medica, Oct. 2015, p. 558, Shanghai, China published.

Majimbi, Maimuna, et al. "Sodium alginate microencapsulation improves the short-term oral bioavailability of cannabidiol when administered with deoxycholic acid", Plos one; Jun. 17, 2021; pp. 1-11.

* cited by examiner

*Primary Examiner* — Zohreh A Fay
(74) *Attorney, Agent, or Firm* — MUNCY, GEISSLER, OLDS & LOWE, P.C.

(57) ABSTRACT

Provided is a spinning solution, comprising a cannabidiol powder and an alginate solution. Besides, the present invention further provides an alginate fiber comprising cannabidiol, and the preparation method and the use thereof. The cannabidiol powder in the spinning solution can be evenly dispersed in the alginate solution, so that the spinning solution of the present invention can be applied to wet spinning to form the alginate fiber comprising cannabidiol. The alginate fiber comprising cannabidiol has anti-oxidative, anti-bacterial, anti-inflammatory, and anti-allergic abilities.

5 Claims, 5 Drawing Sheets

SPINNING SOLUTION, AND ALGINATE FIBER COMPRISING CANNABIDIOL, METHOD FOR PRODUCING THE SAME, AND USE THEREOF

CROSS REFERENCE

Pursuant to 35 U.S.C. § 119(a), this application claims the benefit of the priority to Taiwan Patent Application No. 110140458, filed on Oct. 29, 2021. The content of the prior application is incorporated herein by its entirety.

BACKGROUND OF THE INVENTION

1. FIELD OF THE INVENTION

The present invention relates to a spinning solution, and particularly to a spinning solution comprising cannabidiol powder. Besides, the present invention relates to a fiber, particularly to a fiber comprising cannabidiol (CBD), the method for producing the fiber and the use thereof.

2. DESCRIPTION OF THE PRIOR ARTS

Current demands of consumers for clothing and home accessories have changed along with the changes of consumption pattern and lifestyle, from pursuing aesthetics only, to pursing both aesthetics and functionality. The common functions of functional textile comprise anti-bacteria activity, anti-dust mite activity, anti-ultraviolet activity, sweat wicking, temperature managing, drag reducing and pain alleviating during extreme sport, and the like.

CBD can be used for treating chronic pain, anxiety and insomnia, and it is a potential substance for adding to fibers for production of functional textiles. However, CBD is liposoluble and its solubility in water is only $6.3\times10^{-5}$ mg/mL (see Benedette Cuffari, 2020, Improving the Water Solubility of CBD for Cancer Treatment). Therefore, when trying to produce a fiber with CBD for manufacturing common textiles such as clothing, towels, sheets, duvet covers and masks, in order to utilize CBD's functionality such as anti-anxiety or treating insomnia in daily life, it would be difficult due to the low solubility of CBD in an aqueous solvent used in wet spinning.

SUMMARY OF THE INVENTION

In light of the fact that the current technology cannot effectively produce a fiber comprising CBD by wet spinning with an aqueous solvent, the present invention provides a spinning solution, which makes CBD dispersed evenly in the aqueous solvent and can be used for wet spinning. Therefore, a fiber, a yarn or a textile comprising CBD can be produced and can be applied in daily life.

To achieve the above purpose, the present invention provides a spinning solution comprising a CBD powder and an alginate solution.

The spinning solution comprises the alginate solution, so that the high molecular weight long chain of alginate can induce steric hindrance, which allows particles of the CBD powder to disperse evenly in the alginate solution. This prevents the CBD powder from aggregation and precipitation. Therefore, the difficulties of applicability of CBD in wet spinning due to its low solubility in an aqueous solvent are overcome.

According to the present invention, the alginate solution is an alginate salt solution.

Preferably, a concertation of the alginate solution is 1 wt % to 10 wt %. This concentration range of the alginate solution is good for fiber formation, and the produced fiber has good physical properties and better spinnability. More preferably, a concertation of the alginate solution is 1.5 wt % to 7.5 wt %. More preferably, a concertation of the alginate solution is 2 wt % to 5 wt %.

Preferably, a weight ratio of the alginate solution and the CBD powder is from 75 to 99.99:0.01 to 25. The CBD powder within this ratio range allows the produced fiber to have better spinnability. More preferably, a weight ratio of the alginate solution and the CBD powder is from 80 to 99.9:0.1 to 20. More preferably, a weight ratio of the alginate solution and the CBD powder is 99.9:0.1 to 4.5:1. For example, a weight ratio of the alginate solution and the CBD powder is 5:1. More preferably, a weight ratio of the alginate solution and the CBD powder is 99.9:0.1 to 50:1. More preferably, a weight ratio of the alginate solution and the CBD powder is 99.9:0.1 to 20:1. More preferably, a weight ratio of the alginate solution and the CBD powder is 99.9:0.1 to 95:5.

Preferably, a weight ratio of the alginate and the CBD powder in the spinning solution comprising CBD is 99.9:0.1 to 0.3:1. For example, a weight ratio of the alginate and the CBD powder in the spinning solution comprising CBD is 250:1 to 180:1. More preferably, a weight ratio of the alginate and the CBD powder in the spinning solution comprising CBD is 99.9:0.1 to 0.5:1. More preferably, a weight ratio of the alginate and the CBD powder in the spinning solution comprising CBD is 99.9:0.1 to 0.8:1. More preferably, a weight ratio of the alginate and the CBD powder in the spinning solution comprising CBD is 99.9:0.1 to 4.5:1. More preferably, a weight ratio of the alginate and the CBD powder in the spinning solution comprising CBD is 99.9:0.1 to 50:1. More preferably, a weight ratio of the alginate and the CBD powder in the spinning solution comprising CBD is 99.9:0.1 to 20:1. More preferably, a weight ratio of the alginate and the CBD powder in the spinning solution comprising CBD is 99.9:0.1 to 95:5

Preferably, an average particle diameter of the CBD powder is from 300 nanometers (nm) to 600 nm. More preferably, an average diameter of the CBD powder is from 350 nm to 590 nm. More preferably, an average diameter of the CBD powder is from 380 nm to 580 nm. The particles of the CBD powder in this diameter range allow the CBD powder to disperse more evenly in the alginate solution, which is beneficial for producing fiber through wet spinning. In one embodiment, an average particle diameter of the CBD powder is 456 nm. In the other embodiment, an average particle diameter of the CBD powders is 392 nm. In another embodiment, an average particle diameter of the CBD powder is 578.6 nm.

Preferably, the alginate can be sodium alginate, potassium alginate, calcium alginate, or zinc alginate. More preferably, the alginate is sodium alginate. Specifically, the alginate is a polysaccharide salt, which is formed by crosslinking D-mannuronic acid and L-guluronic acid, wherein the amount ratio of D-mannuronic acid and L-guluronic acid is from 1:2 to 2:1. Preferably, the amount ratio of D-mannuronic acid and L-guluronic acid is 1:1.

The present invention further provides a method for producing an alginate fiber comprising CBD, comprising: step (A) wet spinning the aforementioned spinning solution to form the alginate fiber comprising CBD.

Preferably, said step (A) is step (A') introducing the spinning solution into a coagulation solution through a spinneret to form the alginate fiber comprising CBD, wherein the coagulation solution comprises calcium chloride and water, wherein a weight ratio of the calcium chloride and the water is from 1 to 10:90 to 99. More preferably, a weight ratio of the calcium chloride and the water is from 3 to 7:93 to 97.

Preferably, the coagulation solution further comprises an alcohol, wherein a weight ratio of the calcium chloride, the water and the alcohol is 1 to 10:40 to 50:40 to 50. More preferably, a weight ratio of the calcium chloride, the water and the alcohol is 3 to 7:45 to 48:45 to 48. More preferably, the alcohol is a lower alcohol, such as ethanol or propylene glycol.

More preferably, a temperature of the coagulation solution is from 0° C. to 40° C. More preferably, the temperature of the coagulation solution is 25° C.

Preferably, the step (A) of the method for producing the alginate fiber comprising CBD comprises step (A1) passing the spinning solution through a sieve for filtering to obtain a filtered spinning solution; and step (A2) introducing the filtered spinning solution into a coagulation solution through a spinneret to form the alginate fiber comprising CBD.

Preferably, the spinneret has 2000 holes to 5000 holes, wherein a diameter of each hole is from 0.05 millimeters (mm) to 2 mm.

Preferably, the method for producing the alginate fiber comprising CBD further comprises a step (B): water-washing and alcohol-washing the alginate fiber comprising CBD and drying at a temperature of 25° C. to 120° C. to obtain a dried alginate fiber comprising CBD. In one embodiment, the alcohol is methanol. In another embodiment, the alcohol is ethanol. Preferably, the method for producing the alginate fiber comprising CBD further comprises a step (B): water-washing and alcohol-washing the alginate fiber comprising CBD and drying at a temperature of 80° C. to 120° C. to obtain a dried alginate fiber comprising CBD. In one embodiment, the alcohol is methanol. In another embodiment, the alcohol is ethanol.

Preferably, the method for producing the alginate fiber comprising CBD further comprises step (A0) dissolving the CBD powder in ethanol to obtain a CBD alcohol solution, adding the CBD alcohol solution into a protecting agent solution to obtain a CBD dispersion, and adding the CBD dispersion into an alginate solution to obtain the spinning solution. Preferably, the alcohol is ethanol or propylene glycol. The protecting agent solution comprises any of sodium alginate, polyethylene glycol (PEG), polyvinylpyrrolidone (PVP), chitosan, phospholipid, cyclodextran and combinations thereof. In one embodiment, the protecting agent solution is 1 wt % sodium alginate solution.

Preferably, the CBD alcohol solution in step (A0) is added to the protecting agent solution, and the protecting agent solution is agitated at a rotation speed of 10000 rpm to 15000 rpm.

Preferably, the CBD powder of CBD dispersion in step (A0) has a polymer dispersity index (PDI) of 0.4 or lower. More preferably, the PDI of CBD powder is from 0.05 to 0.3. More preferably, the PDI of CBD powder is from 0.1 to 0.25. In one embodiment, the PDI of CBD powder is 0.197. In another embodiment, the PDI of CBD powder is 0.159.

The present invention further provides an alginate fiber comprising CBD, which comprises CBD and an alginate, and the CBD is dispersed in the alginate fiber comprising CBD.

Preferably, a weight ratio of the alginate and the CBD in the alginate fiber comprising CBD is 75 to 99.99:0.01 to 25. Preferably, a weight ratio of the alginate and the CBD in the alginate fiber comprising CBD is 99.9:0.1 to 0.3:1. For example, a weight ratio of the alginate and the CBD in the alginate fiber comprising CBD is 250:1 to 180:1. More preferably, a weight ratio of the alginate and the CBD in the alginate fiber comprising CBD is 80 to 99.9:0.1 to 20. More preferably, a weight ratio of the alginate and the CBD in the alginate fiber comprising CBD is 99.9:0.1 to 0.5:1. More preferably, a weight ratio of the alginate and the CBD in the alginate fiber comprising CBD is 99.9:0.1 to 0.8:1. More preferably, a weight ratio of the alginate and the CBD in the alginate fiber comprising CBD is 99.9:0.1 to 4.5:1. More preferably, a weight ratio of the alginate and the CBD in the alginate fiber comprising CBD is 99.9:0.1 to 50:1. More preferably, a weight ratio of the alginate and the CBD in the alginate fiber comprising CBD is 99.9:0.1 to 20:1. More preferably, a weight ratio of the alginate and the CBD in the alginate fiber comprising CBD is 99.9:0.1 to 95:5.

Preferably, a fineness of the alginate fiber comprising CBD is 3 dtex to 5 dtex. More preferably, a fineness of the alginate fiber comprising CBD is 3.5 dtex to 4.8 dtex.

Preferably, a strength of the alginate fiber comprising CBD is 5 centi-newtons per tex (cN/tex) to 15 cN/tex. More preferably, a strength of the alginate fiber comprising CBD is 7 cN/tex to 14 cN/tex. More preferably, a strength of the alginate fiber comprising CBD is 10 cN/tex to 14 cN/tex.

Preferably, an elongation of the alginate fiber comprising CBD is 7% to 20%. More preferably, an elongation of the alginate fiber comprising CBD is 17.5% to 19.9%.

The present invention further provides a yarn comprising the alginate fiber comprising CBD. For example, the alginate fiber comprising CBD can be twisted with another type of fiber, such as Rayon fiber, by a twisting machine to obtain an alginate yarn comprising CBD.

Preferably, a count of the alginate yarn comprising CBD is 15 to 25. More preferably, a count of the alginate yarn comprising CBD is 17 to 22.

Preferably, a breaking strength of the aforementioned yarn is 300 gram-force (gf) to 600 gf. More preferably, a breaking strength of the aforementioned yarn is 400 gf to 580 gf.

Preferably, an elongation of the aforementioned yarn is 5% to 10%. More preferably, an elongation of the aforementioned yarn is 6% to 8%.

The present invention further provides a textile comprising the aforementioned yarn, which includes, but is not limited to, a garter and a sock.

The present invention further provides a use of the alginate fiber comprising CBD, which is used for anti-oxidative applications.

The present invention further provides a use of the alginate textile comprising CBD for anti-oxidative applications.

The present invention further provides a use of the alginate textile comprising CBD for anti-bacterial applications. In one embodiment, the textile can be applied against *Staphylococcus aureus*.

The present invention further provides a use of the alginate textile comprising CBD for anti-inflammatory application.

The present invention further provides a use of the alginate textile comprising CBD for anti-allergic application.

The benefit of the present invention lies in that the alginate solution allows water-insoluble CBD to be dispersed therein to form a spinning solution, which can be used in the wet spinning to produce the alginate fiber comprising CBD. Said fiber has excellent physical properties and excellent free radical scavenging activity, and can be further used for producing a yarn or a textile such as garter. The produced textile has anti-oxidative, anti-bacterial, anti-inflammatory and anti-allergic activities. Besides, the washing test shows that the produced textile still has certain amount of CBD and still has the anti-oxidative, anti-bacterial, anti-inflammatory and anti-allergic abilities after 20 times of washing. Consequently, the alginate textile comprising CBD has excellent washability.

DETAILED DESCRIPTION OF THE PREFERRED EMBODIMENTS

Preparation Example 1: CBD Dispersing Solution

Figure 1:
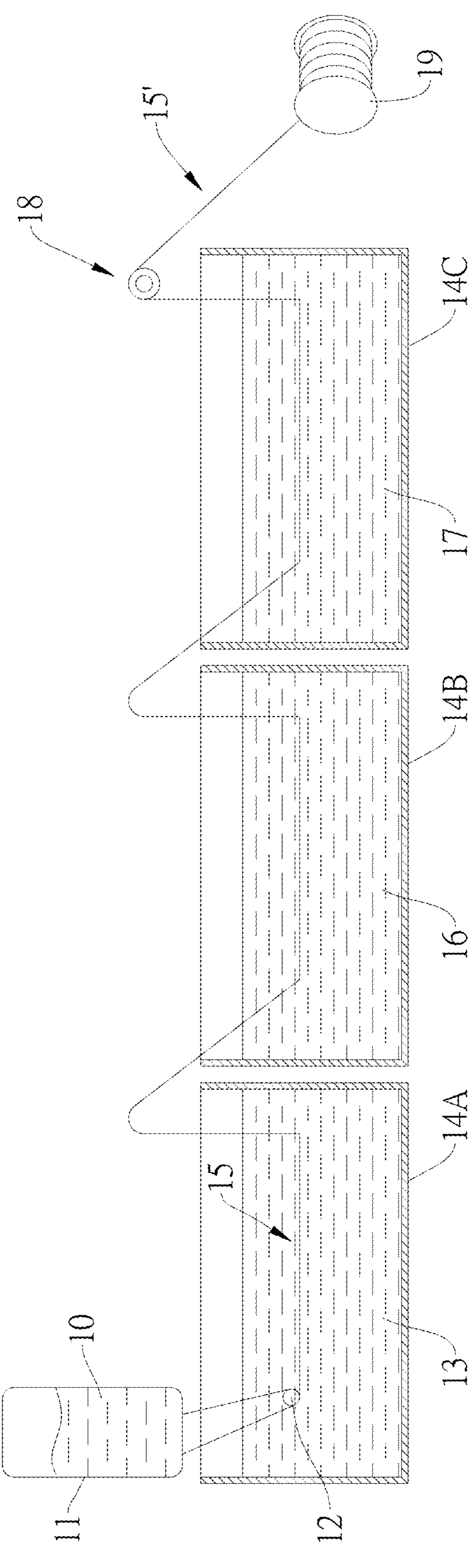
FIG. 1 is a schematic diagram of wet spinning equipment.

A CBD powder was dissolved in an ethanol aqueous solution to obtain a CBD alcohol solution. A weight ratio of ethanol:water:CBD powders in said CBD alcohol solution is 50:50:7.5. The CBD alcohol solution was added to a protecting agent of 1 wt % alginate sodium, while the protecting agent was agitated at a rotation speed of 10000 rpm to 15000 rpm, to obtain a CBD dispersion.

The obtained CBD dispersion was analyzed by Thermogravimetric Analyzer (Kett FD-610) with far infrared radiation at 140° C. for 30 minutes (min). The results showed that the CBD amount in the CBD dispersing solution was 7.5 wt %. In addition, the particle size and size distributions of the CBD powder in the CBD dispersion were determined with a Size analyzer (Malvern nano ZS90) via dynamic light scattering (DLS). The results showed that the z-average size was 456 nm, which represented the hydrated radius of the particles of the CBD powder, and the PDI was 0.197.

Example 1: Spinning Solution

First, a 5 wt % alginate solution was agitated at a rotation speed of 200 rpm to 400 rpm for 4 hours, wherein the alginate was sodium alginate, a polysaccharide salt formed by crosslinking D-mannuronic acid and L-guluronic acid, wherein the amount ratio of D-mannuronic acid and L-guluronic acid was 1:1. The CBD dispersion of Preparation Example 1 was slowly added into the agitated alginate solution followed by agitation at a rotation speed of 200 rpm to 400 rpm for 1 hour. After uniform mixing was achieved, the spinning solution was obtained. The weight ratio of water:alginate:CBD powder in the spinning solution was 95:5:0.25, that is to say, the weight ratio of the alginate:CBD powder was 20:1.

The viscosity of the spinning solution of Example 1 was measured. The result showed that the viscosity was 39000 centipoises (cps) at a rotation speed of 1 rpm. In addition, the aforementioned spinning solution was filtered through a 400 mesh stainless steel sieve, wherein the diameter of the holes on the 400 mesh sieve was about 38 micrometers (μm). There were no powders remaining on the sieve, as observed by naked eyes. Therefore, the particles of the CBD powder were evenly dispersed in the spinning solution of the present Example without forming big aggregates.

Example 2: Spinning Solution

The method for producing the spinning solution of Example 2 was similar to Example 1. The difference lies in that after the CBD dispersion of preparation example 1 was added to the alginate solution, the weight ratio of water:alginate:CBD powders in the obtained spinning solution was 95:5:1, wherein the alginate was sodium alginate. Besides, the viscosity of the spinning solution of the present example was 45000 cps at a rotation speed of 1 rpm. In addition, the spinning solution of the present example was filtered through a 400 mesh stainless steel sieve, wherein the diameter of the holes on the 400 mesh sieve was about 38 μm. There were no powders remaining on the sieve, as observed by naked eyes. Therefore, the particles of the CBD powder were evenly dispersed in the spinning solution of the present Example without forming big aggregations.

Example 3: Spinning Solution

The method for producing the spinning solution of Example 3 was similar to Example 1. The difference lies in that after the CBD dispersion of preparation example 1 was added to the alginate solution, the weight ratio of water:alginate:CBD powders in the obtained spinning solution was 95:5:0.025, wherein the alginate was sodium alginate. Besides, the viscosity of the spinning solution of the present example was 38000 cps at a rotation speed of 1 rpm. In addition, the spinning solution of the present example was filtered through a 400 mesh stainless steel sieve, wherein the diameter of the holes on the 400 mesh sieve was about 38 μm. There were no powders remaining on the sieve, as observed by naked eyes. Therefore, the particles of the CBD powder were evenly dispersed in the spinning solution of the present Example without forming big aggregates.

Examples 4 to 7: Spinning Solutions

The method for producing the spinning solutions of Examples 4 to 7 was similar to Example 1. The difference lies in the weight ratio of water:alginate:CBD powders in the obtained spinning solution after the CBD dispersion of preparation example 1 was added to the alginate solution. The weight ratio of water:alginate:CBD powders of the spinning solutions of Examples 4 to 7 were recorded in the following Table 1. In view of this, the spinning solutions obtained could be used as the test specimens for the following experiments in order to analyze the stability of the spinning solution in continuous spinning.

Experiment 1: Stability of Spinning Solution in Continuous Spinning

The spinning solutions of Examples 4 to 7 were respectively wet spun to test whether the aforementioned spinning solution can be used for continuous spinning for 1 hour without yarn breakage in order to analyze their stability. That is, if the continuous spinning can be conducted for 1 hour, then it is determined as one successful batch. Among them, the test of Example 6 was repeated for 7 times. The results were shown in the following Table 1.

TABLE 1

The stability test of the spinning solutions of Examples 4 to 7

| Test number | group | weight ratio of water: alginate:CBD powders | Spinning time (hr) | accumulation successful batch |
|---|---|---|---|---|
| 1 | Example 4 | 94.525:4.975:0.5 | 1 | 1 |
| 2 | Example 5 | 92.15:4.85:3 | 2 | 2 |
| 3 | Example 6 | 90.25:4.75:5 | 1 | 1 |
| 4 | Example 6 | 90.25:4.75:5 | 3 | 3 |
| 5 | Example 6 | 90.25:4.75:5 | 3 | 3 |
| 6 | Example 6 | 90.25:4.75:5 | 3 | 3 |
| 7 | Example 6 | 90.25:4.75:5 | 3 | 3 |
| 8 | Example 6 | 90.25:4.75:5 | 3 | 3 |
| 9 | Example 6 | 90.25:4.75:5 | 3 | 3 |
| 10 | Example 7 | 76:4:20 | 0.5 | 0 |

According to the above results, the spinning solutions of Examples 4 to 6 can make wet spinning process continuity. That is, the continuous spinning can last for 1 to 3 hours. For Example 7, the spinneret was stuck within half an hour, due to too much CBD content. Even if passing the spinning solution through a 400 mesh stainless steel sieve in advance, the result is the same such that the effect of long time continuous spinning is difficult to reach.

Examples 1A and 2A: Alginate Fibers Comprising CBD

Figure 2:
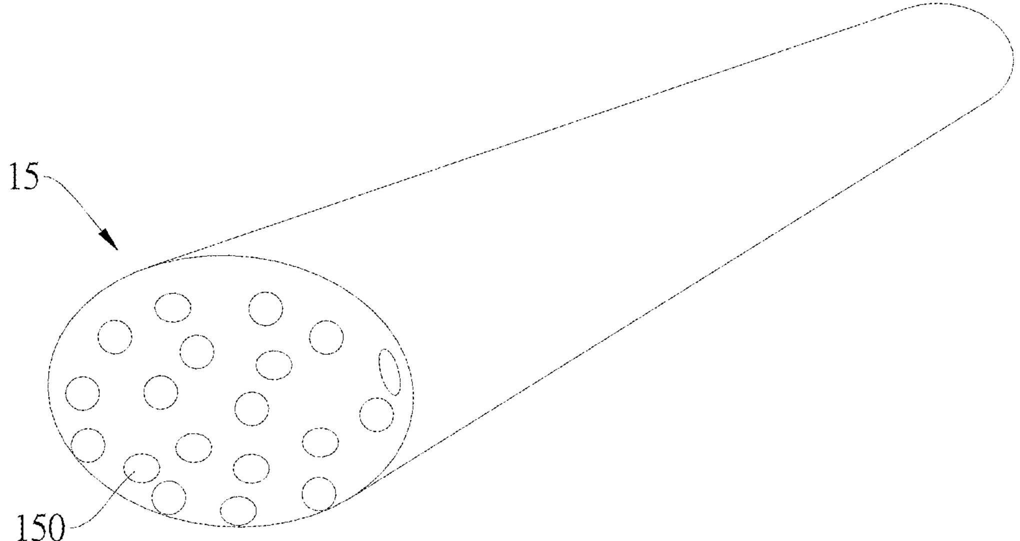
FIG. 2 is a schematic diagram of the alginate fiber comprising CBD.

The spinning solutions of Examples 1 and 2 were wet spun to form alginate fibers of example 1A and example 2A, respectively. Specifically, the spinning solution 10 was de-foamed and then poured into the feeding barrel 11 as shown in FIG. 1. The de-foamed spinning solution was then passed through a spinneret 12 and introduced from the feeding barrel 11 to a coagulation bath 14A containing a coagulation solution 13, wherein the spinneret 12 has 3000 holes (not shown in the figure), and a diameter of each hole was 0.1 mm. The coagulation solution 13 consisted of calcium chloride and water, wherein the weight ratio of the calcium chloride and the water was 5:95. The temperature of coagulation solution was maintained at 25° C. Then an alginate fiber 15 comprising CBD was formed by bonding of calcium ion with alginate and coagulation. As seen in FIG. 2, the CBD 150 was evenly dispersed in the alginate fiber 15 comprising CBD.

The fibers 15 comprising CBD of examples 1A and 2A can further pass through a water washing tank 14B containing water 16 for water washing; then it can further pass through an alcohol washing tank 14C containing alcohol 17 for alcohol washing, wherein the alcohol 17 is ethanol; followed by separating the adhered fibers by air, then drying by the heated roller 18 at a set temperature of 100° C. After aligning, the dried alginate fibers comprising CBD 15' were collected as a bundle on the collector 19.

Example 1A': Alginate Fiber Comprising CBD

The producing method of alginate fiber comprising CBD of Example 1A' was similar to Example 1A. The difference lies in that the solution spinning solution (Example 1) in Example 1A' was passed through the spinneret and introduced into a coagulation solution consisting of calcium chloride, water, and ethanol, wherein the weight ratio of the calcium chloride, the water, and the ethanol was 5:47.5:47.5.

Example 3A': Alginate Fiber Comprising CBD

The producing method of alginate fiber comprising CBD of Example 3A' was similar to Example 1A'. The difference lies in that the alginate fiber comprising CBD of Example 3A' was produced by the spinning solution of Example 3 via wet spinning. Besides, the produced alginate fiber comprising CBD was dried by the roller at a temperature of 25° C.

Experiment 2: Physical Property Tests of Fibers

Examples 1A, 2A, 1A' and 3A' were used as test samples for the following experiments: the fineness, strength and elongation of the alginate fiber comprising CBD were tested according to the method of ASTM 2255. The results were shown in the Table 2 as follows:

TABLE 2

The test results of the physical properties of the alginate fibers comprising CBD of Examples 1A, 2A, 1A' and 3A'.

| Groups | Fineness (dtex) | Strength (cN/tex) | Elongation (%) |
|---|---|---|---|
| Example 1A | 3.72 | 13.7 | 9.8 |
| Example 2A | 4.09 | 7.5 | 8.5 |
| Example 1A' | 4.6 | 10.2 | 19.4 |
| Example 3A' | 4.5 | 10.7 | 17.8 |

It can be seen from the above table that the alginate fibers comprising CBD of Examples 1A, 2A, 1A' and 3A' have appropriate strength and low deformation possibility, and thereby are suitable for producing the textiles for daily life. Among others, Examples 1A, 1A' and 3A' have better strength, which is suitable for yarn spinning. Especially, the elongation of Examples 1A' and 3A' reach 17.5%, which is closer to the common clothing fiber, such as cotton.

Experiment 3: CBD Amount in Fibers

Examples 1A, 2A, 1A' and 3A' were used as test samples for the following experiment: 0.1 gram (g) alginate fibers comprising CBD were respectively ultrasonic extracted by 1 mL CBD extraction solvent 1 for 4 hours and then their absorbance at 286 nm was measured by the spectrophotometer for calculating the CBD amount in the alginate fibers comprising CBD based on a calibration curve. The extraction solvent 1 consisted of 80 parts by weight propylene glycol and 20 parts by weight 10 wt % saline solution (sodium chloride). The results show that Examples 1A, 2A and 3A' have 3.1 wt %, 8.8 wt %, and 0.1 wt % CBD, respectively.

In addition, the extraction solvent 2 consisting of 80 parts by weight of propylene glycol and 20 parts by weight of 2 wt % saline solution was used in the quantitative test for Examples 1A and 1A'. The results show that the Examples 1A and 1A' have 3.1 wt % and 2.9 wt % CBD, respectively.

As the analyzed results of Example 1 by two extraction solvents were the same, it can be found that the concentration of saline solution in the extraction solvent did not affect the extraction result. Besides, it can be found from the analyzed results of Examples 1A and 1A' that the CBD amount in the two alginate fibers comprising CBD produced from two different coagulation solutions were similar. Therefore, whether a coagulation solution containing ethanol or not did not significantly affect the CBD amount in the alginate fiber comprising CBD. As compared to Example 2A, it was found that the analyzed CBD result of Example 1A was closer to the CBD amount added in fiber preparation, so the following tests were conducted by using Example 1A.

Experiment 4: Anti-Oxidative Ability of Fibers

Example 1A was used as a test sample for the following experiment: 0.1 g alginate fibers comprising CBD were ultrasonic extracted by 1 mL CBD extraction solvent 1 (consisting of 80 parts by weight of propylene glycol and 20 parts by weight of 10 wt % saline solution) for 2 hours to give the sample solution of Example 1A. In addition, 0.07 mg/mL CBD solution (100 fold dilution of 7 mg/mL CBD solution, CBD dissolved in the aforementioned solvent) was used as a comparative sample solution, in which this CBD concentration (0.07 mg/mL) is equal to the content of CBD microcapsule used on commercial fabrics. The aforementioned extraction solvent was used as a control sample solution.

5 μL and 10 μL of the sample solution of Example 1A, comparative sample solution, and the control sample solution were separately added to wells of a 96 well plate for anti-oxidative ability test. The free radical scavenging assay was followed by the instruction manual of DPPH assay kit (Biovision, K2078) and the reaction time for the free radical free radical scavenging assay was adjusted according to the instruction manual. 95 μL assay buffer and 100 μL working buffer were added to each well for mixing respectively with all sample solutions, and reacting for 1 hour at room temperature. Then, the absorbance at 517 nm of all sample solutions was measured by a spectrophotometer and used to calculate the free radical scavenging rate by the following formulation based on a standard curve set up by the reference standard Trolox according to the instruction manual.

$$\text{Free radical scavenging rate}=[(Ac-As)/Ac]\times 100$$

Ac: Absorbance of 0 mole Trolox−Absorbance of assay buffer;

As: Absorbance of sample solution−Absorbance of control group

The results were shown in the following Table 3.

TABLE 3

Free radical scavenging rate of the alginate fiber comprising CBD of Example 1A and comparative example

| Groups | Sample solution amount in the well of 96 well plate | Free radical scavenging rate |
|---|---|---|
| Control sample | 5 μL | 0 |
| solution | 10 μL | 0 |
| Comparative sample | 5 μL | 13.4% |
| solution | 10 μL | 23.7% |
| Sample solution of | 5 μL | 31.9% |
| Example 1A | 10 μL | 39.8% |

Therefore, alginate fiber comprising CBD of Example 1A actually scavenged free radical thus had the anti-oxidative ability. Alginate fiber comprising CBD of the present example dissolved out CBD after extraction by the extraction solvent containing sodium ions that simulates sweat, thereby having the anti-oxidative ability. Therefore, the textile made of the alginate fiber comprising CBD of the present example can dissolve out CBD by the sweat of the human body to reach the anti-oxidative ability.

Alginate Yarn Comprising CBD of Example 1B

The alginate fiber comprising CBD of Example 1A was cut into fiber segments having a length of 38 mm and was mixed with rayon fiber to obtain a mixed fiber, which comprised 20 wt % alginate fiber comprising CBD of Example 1A and 80 wt % rayon fiber. The mixed fiber mixture was opened, carded, drew to obtain a yarn that had a twist level of 300 by air spinning.

Experiment 5: Physical Property Test of Yarn

Example 1B was used as a test sample for the following experiment: the yarn count, breaking strength and elongation of alginate fiber comprising CBD were tested according to the method of ASTM 2256. The results were shown in Table 4 as follows:

TABLE 4

The test results of the physical properties of the alginate yarn comprising CBD of Example 1B.

| Group | Count | Break strength (gf) | Elongation (%) |
|---|---|---|---|
| Example 1B | 20.4 | 549.9 | 6.99 |

It can be seen from the above table that the alginate yarn comprising CBD of Example 1B has appropriate break strength and low deformation possibility, and thereby is suitable for producing the textiles for daily life.

Experiment 6: CBD Releasing Test of Yarn Using PBS as Simulated Sweat

Example 1B was used as a test sample for the following experiment: 0.1 g to 0.2 g alginate yarn comprising CBD was added to the 10-fold volume to weight ratio of 1×PBS (NaCl of 8 g/L, KCl of 0.2 g/L, $Na_2HPO_4$ of 1.44 g/L, $KH_2PO_4$ of 2.4 g/L) to give a mixture, and the mixture was ultrasonic agitated for 1 hour at 37° C., and stayed still for 24 hours, followed by 3 times dd water-washing to remove the remaining PBS. The washed alginate yarn was dried at 50° C. for 2 hours and then its absorbance at 286 nm was measured by the spectrophotometer in accordance with the Experiment 3 (using extraction solvent 1) for calculating the remaining CBD amount in the alginate yarn comprising CBD based on a calibration curve. The remaining CBD amount in the alginate yarn comprising CBD was divided by the original CBD amount in the yarn (still for 0 hour) to obtain the CBD remaining percentage.

Figure 3:
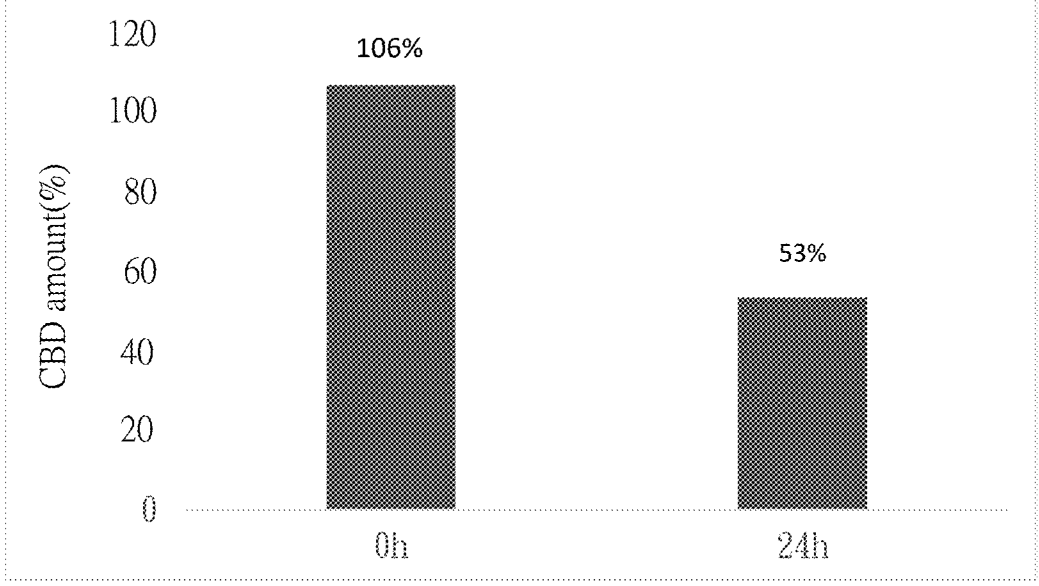
FIG. 3 shows CBD remaining amount of alginate yarn comprising CBD of Example 1B after extracting with phosphate buffered saline (PBS).

The result of CBD remaining percentage of the alginate yarn comprising CBD was shown in FIG. 3. After extraction by PBS comprising sodium ion for 24 hours, the alginate yarn comprising CBD of Example 1B still had CBD of 50% or more. Therefore, it is clear that although the alginate yarn comprising CBD releases CBD by contacting the sweat, a certain CBD amount remains in the yarn.

Alginate Textile Comprising CBD of Example 1C

The alginate yarn comprising CBD of Example 1B was knitted to produce a plain knitted garter having a length of 150 cm by a stocking machine, which was used as Example 1C.

Experiment 7: CBD Releasing Test of Textile Using PBS as Simulated Sweat

Example 1C was used as a test sample for the following experiment:

0.1 g to 0.2 g alginate textile comprising CBD was added to the 10-fold volume to weight ratio of water or PBS to give a mixture, and the mixture was 6 ultrasonic agitated for 1 hour at 37° C., and stayed still for 24 hours, followed by 3 times dd water-washing to remove the remaining PBS. The washed alginate textile was dried at 50° C. for 2 hours and then its absorbance at 286 nm was measured by the spectrophotometer with the Experiment 3 (using extraction solvent 1) for calculating the remaining CBD amount in the alginate textile comprising CBD based on a calibration curve. The remaining CBD amount in the alginate textile comprising CBD was divided by the original CBD amount in the textile (still for 0 hour) to obtain the CBD remaining percentage.

Figure 4:
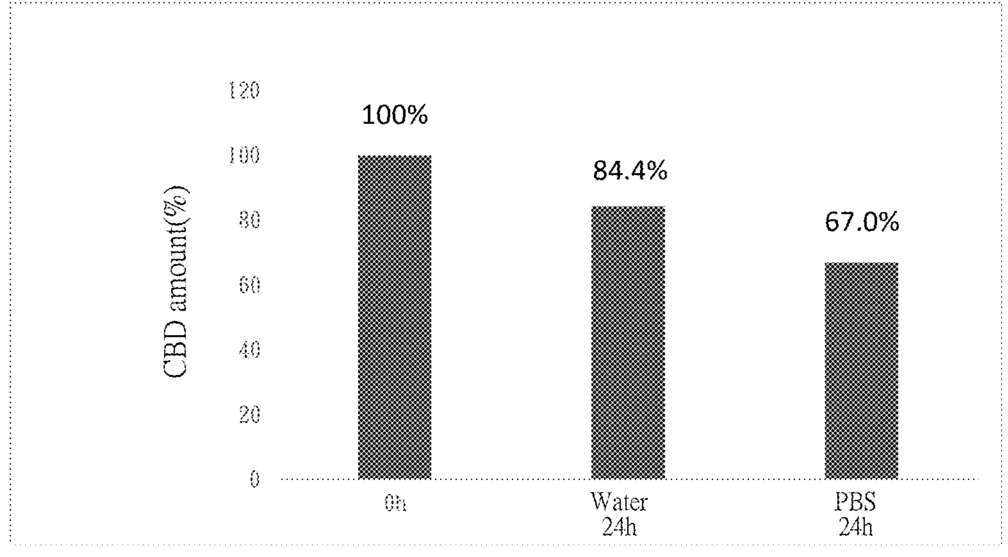
FIG. 4 shows CBD remaining percentage of alginate textile comprising CBD of Example 1C after washing or without washing.

The result of CBD remaining percentage of the alginate textile comprising CBD was shown in FIG. 4. After extraction by water for 24 hours, the alginate textile comprising CBD of Example 1C still had CBD of 84.4%. After extraction by PBS comprising sodium ion, for 24 hours, the alginate textile comprising CBD of Example 1C still had CBD of 67%. Therefore, it is clear that the alginate textile comprising CBD not only released CBD but also maintained certain CBD amount in the yarn.

Experiment 8: CBD Amount in Textile after Washing

Example 1C was used as a test sample for the following experiment: 1.8 kilograms (kg) alginate textile comprising CBD was put in a washing machine (blank cloth can be used to make up for the lack of weight), and the textile and blank cloth were washed according to the standard method of AATCC135, wherein a water level was medium, a water temperature was cold, and a laundry program was regular. 4 pounds (lb) water was used in each washing cycle. 20 cycles were processed either by using 20 mL detergent (Attack EX, KAO), or by washing by water (without the detergent). After washing, the washed textile was ultrasonic extracted by the CBD extraction solvent 1 for 4 hours and then its absorbance at 286 nm was measured by the spectrophotometer for calculating the CBD amount in the alginate textile comprising CBD of Example 1C after 1, 2, 3, 4, 5, 10, 15, and 20 cycles of washing based on the calibration curve. The calculation was conducted as follows:

CBD percentage=[CBD amount after washing (wt %)/CBD amount before washing (wt %)]×100%.

The results were shown in the following Table 5.

TABLE 5

CBD percentage of alginate textile comprising CBD of Example 1C after washing

| Number of Washing cycles | CBD percentage after washing with detergent | CBD percentage after washing with water |
|---|---|---|
| 1 | 26% | Not tested |
| 2 | 26% | Not tested |
| 3 | 25% | Not tested |
| 4 | 18% | Not tested |
| 5 | 19% | 55% |
| 10 | 19% | 56% |
| 15 | 17% | 53% |
| 20 | 17% | 35% |

The results showed that the CBD percentage of alginate textile comprising CBD of Example 1C generally decreased with the number of washing cycles after washing with the detergent, and ¼ CBD amount could remain within the first 3 washing cycles. After that, the CBD amount decreased slightly during $4^{th}$ to $20^{th}$ washing cycles, wherein the CBD percentage can remain at around 17% to 19%. On the other hand, the CBD percentage of alginate textile comprising CBD of Example 1C remained more than 50% after washing by water for up to 15 cycles, and the CBD percentage can remain more than ⅓ after washing by water for 20 cycles. Therefore, the alginate textile comprising CBD of the present example can maintain a certain CBD amount after washing with or without the detergent. This proves that the alginate textile comprising CBD of the present example has good washability.

Experiment 9: Anti-Oxidative Ability of Textile after Water-Wash

Example 1C after washing by water for 20 cycles as mentioned in Experiment 8 and Example 1C not subjected to any washing process were used as test examples for the following experiment: test samples of water-washed group (0.1 g alginate textile comprising CBD after washing by water for 20 cycles as mentioned in Experiment 8), non-water-washed group (0.1 g alginate textile comprising CBD not subjected to any washing process) and blank group (0.1 g alginate textile without CBD) were ultrasonic extracted by 1 mL extraction solvent of the present experiment (DMSO/$H_2O$/NaCl=80/15/5 wt %) for 2 hours. 5 μL solution obtained by the alginate fiber comprising 3% CBD dissolved in the extraction solvent of the present invention was used as a sample solution for CBD group while the extraction solvent of the present invention was used as a sample solution for control group. 5 μL of each sample solution was separately added to wells of a 96 well plate. Each group was performed in duplicate. The free radical scavenging assay was followed by the instruction manual of DPPH assay kit (Biovision, K2078) and the reaction time for the free radical free radical scavenging assay was adjusted according to the instruction manual. 95 μL assay buffer and 100 μL working buffer were added to each well for mixing respectively with all sample solutions and reacting for 1 hour at room temperature. Then, the absorbance at 517 nm of all sample solutions were measured by a spectrophotometer to calculate the free radical scavenging rate by the following formulation based on a standard curve set up by the reference standard Trolox according to the instruction manual.

$$\text{Free radical scavenging rate} = [(Ac - As)/Ac] \times 100$$

Ac: Absorbance of 0 mole Trolox−Absorbance of assay buffer;

As: Absorbance of sample solution−Absorbance of control group

Figure 5:
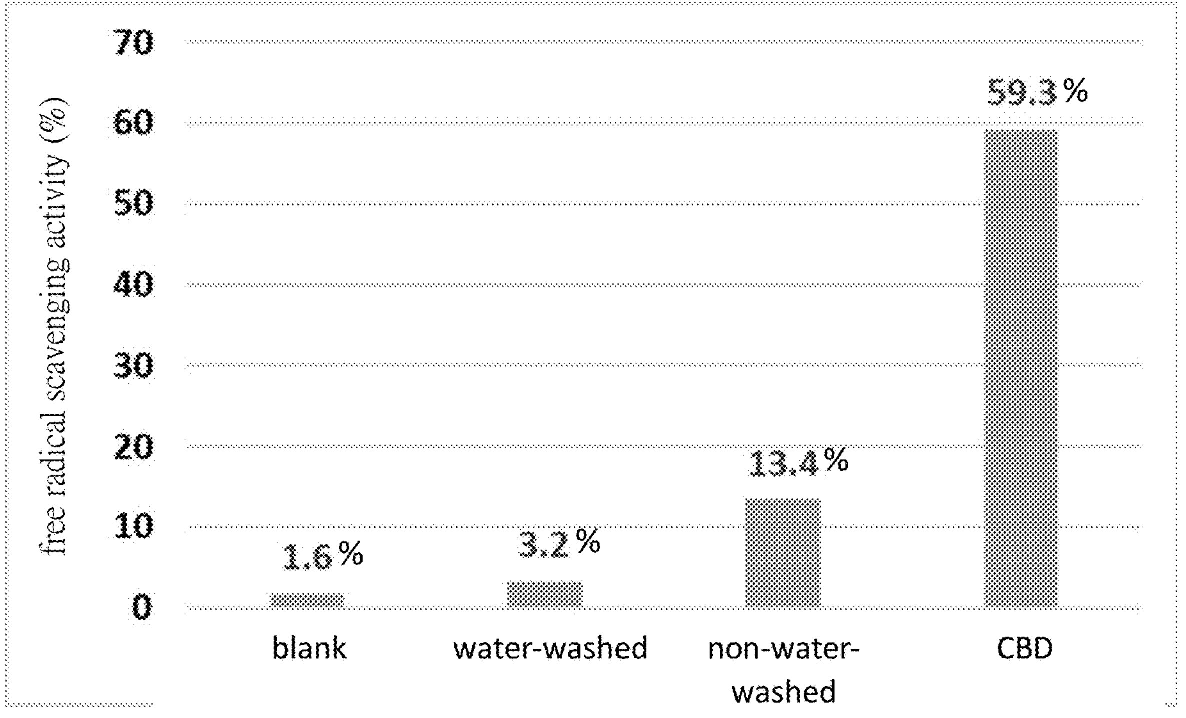
FIG. 5 shows free radical scavenging rate of alginate textile comprising CBD of Example 1C after washing or without washing.

The results were shown in FIG. 5, which showed that the alginate textile comprising CBD of Example 1C actually scavenged free radical thus had the anti-oxidative ability. Besides, after extraction by the extraction solvent simulating sweat comprising sodium ion, the textile dissolved out the CBD it contained, and thus showed the anti-oxidative ability. The alginate textile comprising CBD of Example 1C had ¼ free radical scavenging ability after washing by water for 20 cycles compared to Example 1C not subjected to washing by water. This equals to 2 times of free radical scavenging ability of blank group. Therefore, the alginate textile comprising CBD of the present invention has certain anti-oxidative ability and washability.

Experiment 10: Anti-Bacterial Ability of Textile

Example 1C after washing by water for 20 cycles mentioned in Experiment 8 and Example not subjected to any washing process were used as test examples and were named as water-washed group and non-water-washed group, respectively. Besides, the blank group was used as a control group for the experiment procedure. The anti-*Staphylococcus aureus* (BCRC 10451) ability of test samples were tested according to "JIS L 1902:2015 Determination of Antibacterial Activity and Efficacy of Textile Products." The data of blank group was also provided according to JIS L 1902:2015. The results were shown in the following Table 6.

TABLE 6

The anti-bacterial ability of the alginate textile comprising CBD of Example 1C before and after washing.

| | CFU eluted right after inoculation (CFU/0.4 g) | CFU after 24 hours incubation for (CFU/0.4 g) | Notes |
|---|---|---|---|
| Blank group | $C_0' = 2.90 \times 10^4$ | $C_t' = 4.61 \times 10^6$ | F = 2.2 |
| Control group | $C_0$ = — | $C_t$ = — | |
| Non-water-washed group | $T_0 = 2.77 \times 10^4$ | $T_t$ = ≤20 | G = −3.1<br>A = >5.3 |
| Water-wash group | $T_0 = 2.77 \times 10^4$ | $T_t$ = ≤20 | G = −3.1<br>A = >5.3 |

Formulations of test results were shown as follows:
F (Growth value of control group) = $\log C_t - \log C_0$. If F > 2.0, the test is valid.
G (Growth value of sample group) = $\log T_t - \log T_0$
A (anti-bacterial activity value) = $(\log Ct - \log C_0) - (\log Tt - \log T_0) = F - G$
C0': CFU eluted right after inoculation of blank group
Ct': CFU after 24 hr incubation of blank group
C0: CFU eluted right after inoculation of control group
Ct: CFU after 24 hr incubation of control group
T0: CFU eluted right after inoculation of sample group
Tt: CFU after 24 hr incubation of sample group
Note:
If A (anti-bacterial activity value) >2.0, the sample has anti-bacterial activity for the testing bacterial strain.

The growth value of blank group was 2.2, while the growth value of sample group is-3.1. Both the water-wash group and the non-wash group have anti-bacterial activity value of more than 5.3. Therefore, the alginate textile comprising CBD of Example 1C has anti-bacterial activity, which is not affected by water-wash. Consequently, the alginate textile comprising CBD of Example 1C has good washability.

Experiment 11: Anti-Inflammatory and Anti-Allergic Ability of Textile

Example 1C washing by water for 20 cycles as mentioned in Experiment 8 and Example 1C not subjected to any washing process were used as test examples for the following experiment: test samples of water-washed group (0.1 g alginate textile comprising CBD after washing by water for 20 cycles as mentioned in Experiment 8), non-water-washed group (0.1 g alginate textile comprising CBD not subjected to any washing process) and blank group (0.1 g alginate textile without CBD) were ultrasonic extracted by 1 mL extraction solvent of the present experiment ($DMSO/H_2O/NaCl$=80/15/5 wt %) for 2 hours. 5 μL solution obtained by the alginate fiber comprising 3% CBD dissolved in the extraction solvent of the present invention was used as a sample solution for CBD group. Mouse macrophage cells (RAW 264.7, from Bioresource Collection and Research Center) were seeded into wells of three 24-well plates with a density of 100,000 cells/well. After 24 hours incubation, each well was added with lipopolysaccharide (LPS) to reach a concentration of 1 μg/mL for inducing cell inflammation for 60 minutes. Then each well was added with 20 μL of sample solution of each group. At the meantime, there was a non-addition group, which contained no sample solution or solvent. After 24 hours incubation, the supernatants of cultured cells were collected and frozen at −80° C., and the absorbance at 520 nm of the supernatants was measured for calculating nitrate amount by the following formulation based on a standard curve of nitrate according to the instruction manual of Nitric Oxide Colorimetric Assay Kit (Bio Vision, #K262-200) but the absorbance reading was adjusted to 520 nm:

{[(sample absorbance−control absorbance)−intercept of the standard curve]/slope of the standard curve}/(sample volume)

The converted nitrate concentration reflected the concentration of nitric oxide. In addition, the control group was formulated according to the instruction manual, which consisted of supernatant of each group and the assays buffer without the assay enzyme in the kit.

The results were shown in the following Table 7:

TABLE 7

The nitrate concentration of alginate textile comprising CBD of Example 1C before and after washing.

| Groups | nitrate concentration (μM) |
|---|---|
| non-addition group | 7.11 |
| Blank sample group | 2.72 |
| Water-washed group | Not detected (lower than the detection limit) |
| Non-water-washed group | Not detected (lower than the detection limit) |
| CBD group | Not detected (lower than the detection limit) |

It can be seen from Table 7 that both the alginate textile comprising CBD of Example 1C in water-wash group and non-wash group had same nitric oxide reduction ability as the CBD group. That is, both groups significantly reduced the nitric oxide produced by the LPS, so the alginate textile comprising CBD of Example 1C can be used for anti-inflammatory and anti-allergic applications. Therefore, anti-inflammatory and anti-allergic abilities of the textile comprising CBD of Example 1C were almost not be affected by washing. That is, the textile comprising CBD of Example 1C has good washability.

To sum up, the alginate fiber comprising CBD of the present invention has enough strength and low deformation possibility and releases CBD in the sweat simulation experiment and actually scavenges the free radicals, has anti-oxidative ability, anti-bacterial, anti-inflammatory, and anti-allergic ability. The textile manufactured by the alginate fiber comprising CBD of the present invention has appropriate break strength and low deformation possibility, and actually has anti-oxidative ability, anti-bacterial, anti-inflammatory, and anti-allergic abilities and washability.

What is claimed is:

1. A method for producing an alginate fiber comprising cannabidiol, the method comprising introducing a spinning solution into a coagulation solution through a spinneret to undergo wet spinning, so as to form the alginate fiber comprising cannabidiol;

wherein the coagulation solution comprises calcium chloride and water, and the spinning solution comprises a cannabidiol powder and an alginate solution;

wherein an average particle diameter of the cannabidiol powder is from 300 nm to 600 nm; a concertation of the alginate solution is from 1 wt % to 10 wt %; and a weight ratio of the alginate solution and the cannabidiol powder is from 75 to 99.99:0.01 to 25;

wherein the alginate is a polysaccharide salt, which is formed by crosslinking D-mannuronic acid and L-guluronic acid.

2. The method according to claim 1, wherein a weight ratio of the calcium chloride and the water is from 1 to 10:90 to 99.

3. The method according to claim 1, wherein the coagulation solution further comprises an alcohol, wherein a weight ratio of the calcium chloride, the water and the alcohol is from 1 to 10:40 to 50:40 to 50.

4. The method according to claim 1, wherein the method comprises a step of passing the spinning solution through a sieve for filtering to obtain a filtered spinning solution before introducing the spinning solution into the coagulation solution through the spinneret to form the alginate fiber comprising cannabidiol, wherein the spinning solution is the filtered spinning solution.

5. The method according to claim 1, wherein the method further comprises: water-washing, alcohol-washing, and drying the alginate fiber comprising cannabidiol at a temperature of 25° C. to 120° C. to obtain a dried alginate fiber comprising cannabidiol.

* * * * *